US00PP35940P2

(12) United States Plant Patent
Kobayashi

(10) Patent No.: US PP35,940 P2
(45) Date of Patent: Jul. 2, 2024

(54) **NEW GUINEA *IMPATIENS* PLANT NAMED 'DONGIPETFIR 23'**

(50) Latin Name: *Impatiens hawkeri*
Varietal Denomination: Dongipetfir 23

(71) Applicant: DUMMEN GROUP B.V., De Lier (NL)

(72) Inventor: Ruth Kobayashi, Carlsbad, CA (US)

(73) Assignee: DÜMMEN GROUP B.V., De Lier (NL)

( * ) Notice: Subject to any disclaimer, the term of this patent is extended or adjusted under 35 U.S.C. 154(b) by 0 days.

(21) Appl. No.: 18/143,486

(22) Filed: May 4, 2023

(51) Int. Cl.
*A01H 5/02* (2018.01)
*A01H 6/16* (2018.01)

(52) U.S. Cl.
USPC ..... Plt./318.7

(58) Field of Classification Search
USPC ..... Plt./317, 318.1, 318.3, 318.7
See application file for complete search history.

(56) References Cited

PUBLICATIONS https://na.dummenorange.com/app/pdfcatalogs/detail.web?catalogId=225; Retrieved from the Internet on Aug. 29, 2023 (2 pages total).*

* cited by examiner

*Primary Examiner* — Susan McCormick Ewoldt
(74) *Attorney, Agent, or Firm* — C. Anne Whealy

(57) ABSTRACT

A new and distinct cultivar of *Impatiens* plant named 'Dongipetfir 23' characterized by its relatively compact, upright to outwardly spreading and mounding plant habit; moderately vigorous growth habit; freely branching habit; dense and full appearance; dark green-colored leaves; freely and early flowering habit; medium-sized single-type reddish orange-colored flowers; and good garden performance.

2 Drawing Sheets

Figure 1:
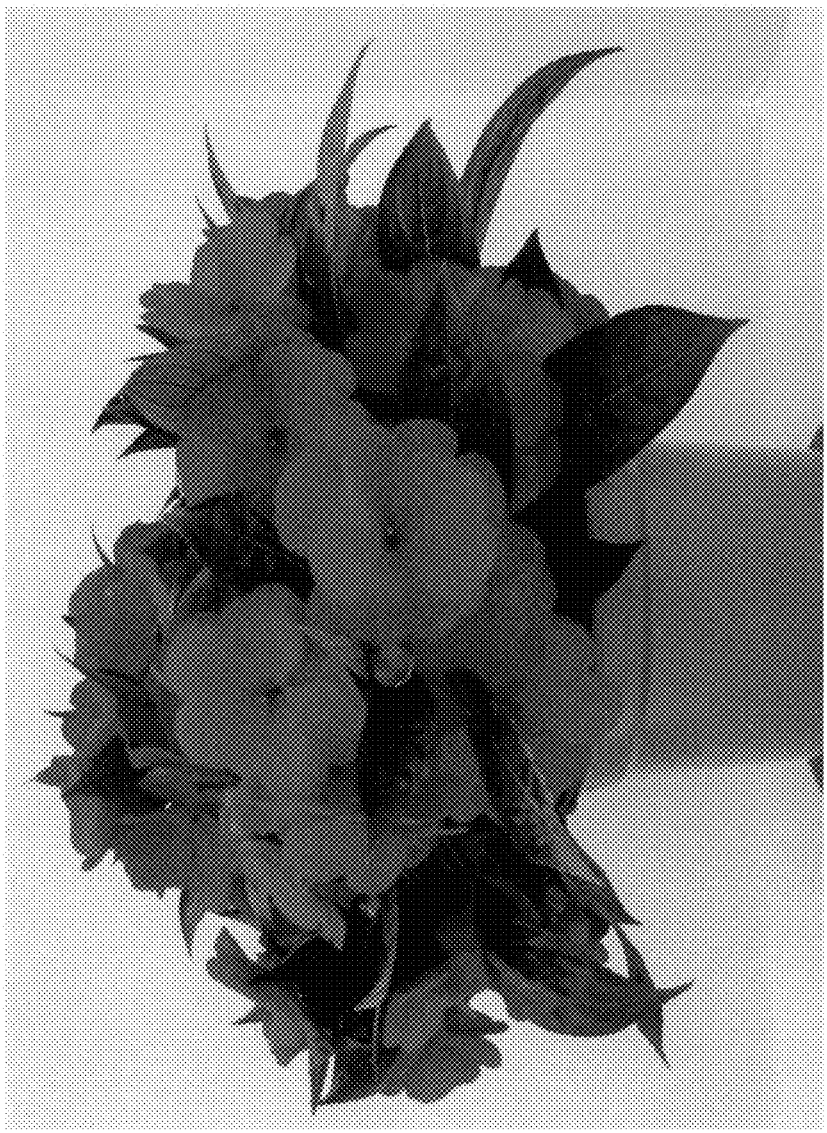

Botanical designation: *Impatiens hawkeri.*
Cultivar denomination: 'DONGIPETFIR 23'.

BACKGROUND OF THE INVENTION

The present invention relates to a new and distinct cultivar of New Guinea *Impatiens* plant, botanically known as *Impatiens hawkeri* and hereinafter referred to by the name 'Dongipetfir 23'.

The new *Impatiens* plant is a product of a planned breeding program conducted by the Inventor in Koka, Ethiopia and Encinitas, California. The objective of the breeding program is to create new freely-branching, early and freely flowering New Guinea *Impatiens* plants with large attractive flowers and good garden performance.

The new *Impatiens* plant originated from a cross-pollination made by the Inventor in November, 2019 in Koka, Ethiopia of a proprietary selection of *Impatiens hawkeri* identified as code number NN17-679683-011, not patented, as the female, or seed, parent with a proprietary selection of *Impatiens hawkeri* identified as code number NN17-604538-002, not patented, as the male, or pollen, parent. The new *Impatiens* plant was discovered and selected by the Inventor as a single flowering plant from within the progeny of the stated cross-pollination in a controlled greenhouse environment in Encinitas, California in April, 2020.

Asexual reproduction of the new *Impatiens* plant by terminal vegetative cuttings in a controlled greenhouse environment in Encinitas, California since June, 2020 has shown that the unique features of this new *Impatiens* plant are stable and reproduced true to type in successive generations.

SUMMARY OF THE INVENTION

Plants of the new *Impatiens* have not been observed under all possible combinations of environmental conditions and cultural practices. The phenotype may vary somewhat with variations in environmental conditions such as temperature, daylight and light intensity without, however, any variance in genotype.

The following traits have been repeatedly observed and are determined to be the unique characteristics of 'Dongipetfir 23'. These characteristics in combination distinguish 'Dongipetfir 23' as a new and distinct *Impatiens* plant:

1. Relatively compact, upright to outwardly spreading and mounding plant habit.
2. Moderately vigorous growth habit.
3. Freely branching habit; dense and full appearance.
4. Dark green-colored leaves.
5. Freely and early flowering habit.
6. Medium-sized single-type reddish orange-colored flowers.
7. Good garden performance.

Plants of the new *Impatiens* can be compared to plants of the female parent selection. Plants of the new *Impatiens* differ primarily from plants of the female parent selection in the following characteristics:

1. Plants of the new *Impatiens* are more mounding than and not as spreading as plants of the female parent selection.
2. Flowers of plants of the new *Impatiens* are reddish orange in color whereas flowers of plants of the female parent selection are orange in color.

Plants of the new *Impatiens* can be compared to plants of the male parent selection. Plants of the new *Impatiens* differ primarily from plants of the male parent selection in the following characteristics:

1. Plants of the new *Impatiens* are not as vigorous as plants of the male parent selection.

2. Plants of the new *Impatiens* are more mounding than and not as spreading as plants of the male parent selection.
3. Plants of the new *Impatiens* have smaller flowers than plants of the male parent selection.
4. Flowers of plants of the new *Impatiens* are reddish orange in color whereas flowers of plants of the male parent selection are orange in color.

Plants of the new *Impatiens* can be compared to plants of *Impatiens hawkeri* 'Timor', disclosed in U.S. Plant Pat. No. 9,144. In side-by-side comparisons, plants of the new *Impatiens* differ primarily from plants of 'Timor' in the following characteristics:

1. Plants of the new *Impatiens* have larger flowers than plants of 'Timor'.
2. Flowers of plants of the new *Impatiens* are reddish orange in color whereas flowers of plants of 'Timor' are bright orange in color.

Plants of the new *Impatiens* can also be compared to plants of *Impatiens hawkeri* 'Duemagwis', disclosed in U.S. Plant Pat. No. 26,782. In side-by-side comparisons, plants of the new *Impatiens* differ primarily from plants of 'Duemagwis' in the following characteristics:

1. Plants of the new *Impatiens* are more mounding than plants of 'Duemagwis'.
2. Plants of the new *Impatiens* have smaller flowers than plants of 'Duemagwis'.
3. Flowers of plants of the new *Impatiens* are reddish orange in color whereas flowers of plants of 'Duemagwis' are light red in color.

BRIEF DESCRIPTION OF THE PHOTOGRAPHS

The accompanying colored photographs illustrate the overall appearance of the new *Impatiens* plant showing the colors as true as it is reasonably possible to obtain in colored reproductions of this type. Colors in the photographs may differ slightly from the color values cited in the detailed botanical description which accurately describe the colors of the new *Impatiens* plant.

The photograph on the first sheet (FIG. 1) is a side perspective view of a typical flowering plant of 'Dongipetfir 23' grown in a container.

Figure 2:
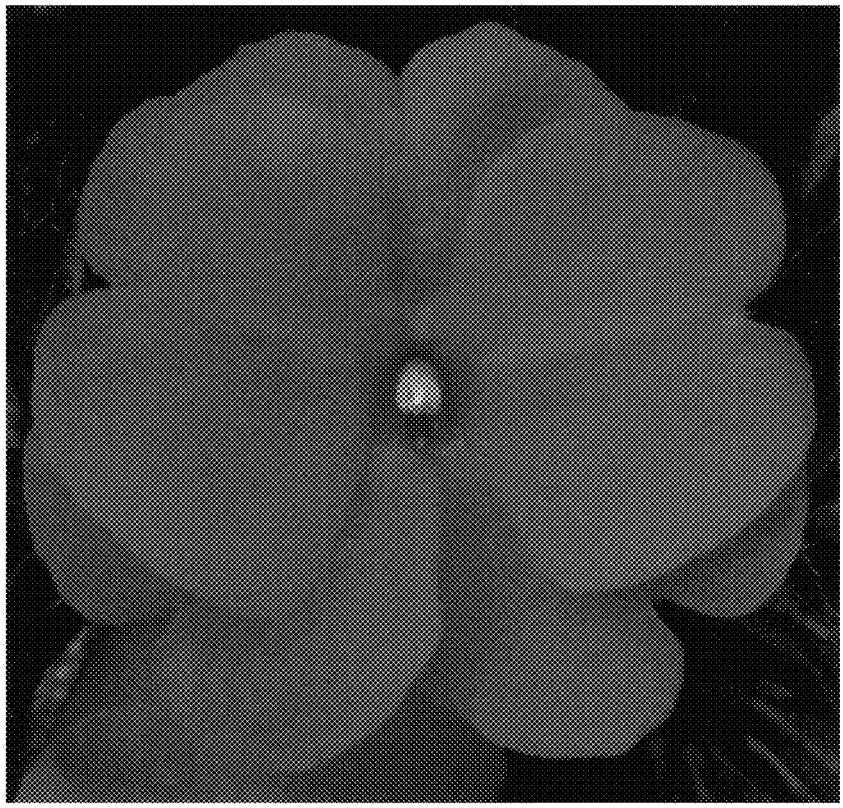

The photograph on the second sheet (FIG. 2) is a close-up view of a typical flower of 'Dongipetfir 23'.

DETAILED BOTANICAL DESCRIPTION

The aforementioned photographs and following observations, measurements and values describe plants grown during the summer in 16.5-cm containers in a polyethylene-covered greenhouse in Encinitas, California and under cultural practices typical of commercial New Guinea *Impatiens* production. During the production of the plants, day temperatures averaged 25 C, night temperatures averaged 18 C and light levels ranged from 4,000 to 4,500 lux. Plants were 16 weeks old when the photographs were taken and 14 weeks old when the description was taken. In the following description, color references are made to The Royal Horticultural Society Colour Chart, 2015 Edition, except where general terms of ordinary dictionary significance are used.

Botanical classification: *Impatiens hawkeri* 'Dongipetfir 23'.

Parentage:

*Female, or seed, parent*.—Proprietary selection of *Impatiens hawkeri* identified as code number NN17-679683-011, not patented.

*Male, or pollen, parent*.—Proprietary selection of *Impatiens hawkeri* identified as code number NN17-604538-002, not patented.

Propagation:

*Type*.—By terminal vegetative cuttings.

*Time to initiate roots, summer and winter*.—About five to seven days at temperatures about 27 C and night temperatures about 20 C.

*Time to produce a rooted young plant, summer and winter*.—About three weeks at day temperatures about 27 C and night temperatures about 20 C.

*Root description*.—Fine, fibrous; typically white in color, actual color of the roots is dependent on substrate composition, water quality, fertilizers, substrate temperature and age of roots.

*Rooting habit*.—Freely branching; dense.

Plant description:

*Plant and growth habit*.—Relatively compact, upright to outwardly spreading and mounding plant habit; broad inverted triangle in overall shape; freely branching habit with lateral branches potentially developing at every node; dense and full appearance; moderately vigorous growth habit and moderate to rapid growth rate.

*Plant height*.—About 21 cm.

*Plant diameter*.—About 41 cm.

Lateral branch description:

*Length*.—About 16 cm.

*Diameter*.—About 9 mm.

*Internode length*.—About 4 cm to 4.5 cm.

*Strength*.—Strong; flexible.

*Aspect*.—Initially upright to outwardly spreading.

*Texture and luster*.—Smooth, glabrous; moderately glossy.

*Color, developing*.—Close to 148A variably overlain with close to 183A.

*Color, developed*.—Close to 148A variably overlain with close to 183A and 187A.

Leaf description:

*Arrangement*.—Typically alternate or in whorls; simple.

*Length*.—About 10.5 cm to 12 cm.

*Width*.—About 3.75 cm to 4.5 cm.

*Shape*.—Elliptic.

*Apex*.—Acuminate.

*Base*.—Cuneate.

*Margin*.—Serrate with ciliation.

*Texture and luster, upper and lower surfaces*.—Smooth, glabrous; moderately glossy.

*Venation pattern*.—Pinnate; arcuate.

*Color*.—Developing and fully expanded leaves, upper surface: Close to between 147A and N189A; midvein proximally, close to 144A variably overlain with close to 61A and 60A, and distally, close to 144A; lateral venation, close to 60A. Developing and fully expanded leaves, lower surface: Close to 147B; midvein proximally, close to 60A, and distally, close to 144A; lateral venation, close to 59A.

*Petiole length*.—About 2.5 cm to 3 cm.

*Petiole diameter*.—About 3 mm to 3.5 mm.

*Petiole texture and luster, upper and lower surfaces*.—Smooth, glabrous; moderately glossy.

*Petiole color, upper surface*.—Close to 60A.

*Petiole color, lower surface*.—Close to 59A.

Flower description:

*Flower type and flowering habit*.—Single-type, medium-sized rounded axillary flowers; freely flowering habit, typically about nine to twelve flower buds and open flowers per lateral branch; flowers positioned above and beyond the foliar plane, flowers typically face mostly upright to outwardly.

*Flower longevity*.—Flowers typically last about four to seven days on the plant under greenhouse conditions; petals self-cleaning, gynoecium persistent.

*Fragrance*.—None detected.

*Natural flowering season*.—Year-round under greenhouse conditions; in the garden, flowering from spring until fall in California; early flowering habit, plants typically begin flowering about ten weeks after planting.

*Flower buds*.—Length: About 1.4 cm. Diameter: About 6 mm. Shape: Ovoid. Texture and luster: Smooth, glabrous; somewhat glossy. Color: Close to 44B.

*Flower diameter*.—About 6 cm by 6.25 cm.

*Flower depth*.—About 1.1 cm.

*Petals*.—Quantity and arrangement: Five per flower in a single whorl. Length, banner petals: About 3 cm. Length, lateral petals: About 2.5 cm. Length, lower petals: About 2.6 cm. Width, banner petal: About 3.75 cm. Width, lateral petals: About 3.3 cm. Width, lower petals: About 3.3 cm. Shape, all petals: Cordate to obcordate. Apex, all petals: Entire or emarginate. Base, all petals: Cuneate. Margin, all petals: Entire; slightly undulate. Texture and luster, all petals, upper surface: Smooth, glabrous; velvety; slightly glossy; iridescent. Texture and luster, all petals, lower surface: Smooth, glabrous; slightly glossy. Color, all petals: When opening and fully opened, upper surface: Close to 44B; towards and at the center, slightly tinged with close to 53A; venation, similar to lamina colors; colors do not change with subsequent development. When opening and fully opened, lower surface: Close to 44C; midvein, banner petal, close to 146A; midvein, lateral and lower petals, close to 44A; colors do not change with subsequent development.

*Sepals*.—Quantity and arrangement: Three in a single whorl; one modified into an elongated spur. Lateral sepal length: About 2.5 mm. Lateral sepal width: About 1 mm. Spur sepal length: About 2 cm. Spur sepal width: About 7 mm. Sepal shape: Deltoid. Sepal apex: Acuminate. Sepal base: Truncate. Sepal margin: Entire. Sepal texture and luster, upper and lower surfaces: Smooth, glabrous; slightly glossy. Sepal color, upper and lower surfaces: Translucent, close to 157A; towards the base, tinged with close to 60A. Spur length: About 3.25 cm. Spur diameter: At flower, about 2.5 mm; at apex, less than 1 mm. Spur shape: Acicular. Spur texture and luster: Smooth, glabrous; moderately glossy. Spur color: Close to 60A.

*Peduncles*.—Length: About 4 cm to 5.5 cm. Diameter: About 2 mm. Angle: About 45 degrees from stem axis. Strength: Strong; flexible. Texture and luster: Smooth, glabrous; somewhat glossy. Color: Close to 148A variably overlain with close to 60A.

*Reproductive organs*.—Stamens: Quantity: Five fused at anthers; filaments free. Anther size: About 1 mm by 0.6 mm. Anther shape: Oblong. Anther color: Close to N155B. Pollen amount: None observed. Pistils: Quantity per flower: One. Pistil length: About 2.5 mm. Stigma shape: Crested. Stigma color: Close to 144A. Style color: Close to 144A. Ovary color: Close to 144A.

*Seeds and fruits*.—To date, seed and fruit production has not been observed on plants of the new *Impatiens*.

Pathogen & pest resistance: To date, plants of the new *Impatiens* have not been observed to be resistant to pathogens and pests common to *Impatiens* plants.

Garden performance: Plants of the new *Impatiens* have been observed to have good garden performance and tolerate temperatures ranging from about 5 C to about 40 C.

It is claimed:

1. A new and distinct *Impatiens* plant named 'Dongipetfir 23' as illustrated and described.

* * * * *